United States Patent
Pedersen et al.

(10) Patent No.: US 10,195,359 B2
(45) Date of Patent: Feb. 5, 2019

(54) DIAL-DOWN MECHANISM FOR WIND-UP PEN

(71) Applicant: Novo Nordisk A/S, Bagsvaerd (DK)

(72) Inventors: Simon Munch Pedersen, Copenhagen (DK); Simon Roervig, Copenhagen (DK)

(73) Assignee: Novo Nordisk A/S, Bagsvaerd (DK)

(*) Notice: Subject to any disclaimer, the term of this patent is extended or adjusted under 35 U.S.C. 154(b) by 220 days.

(21) Appl. No.: 14/403,640

(22) PCT Filed: Mar. 15, 2013

(86) PCT No.: PCT/EP2013/055403
§ 371 (c)(1),
(2) Date: Nov. 25, 2014

(87) PCT Pub. No.: WO2013/178372
PCT Pub. Date: Dec. 5, 2013

(65) Prior Publication Data
US 2015/0148750 A1    May 28, 2015

Related U.S. Application Data

(60) Provisional application No. 61/656,345, filed on Jun. 6, 2012.

(30) Foreign Application Priority Data

May 31, 2012 (EP) .................... 12170139

(51) Int. Cl.
*A61M 5/315* (2006.01)
*A61M 5/20* (2006.01)

(52) U.S. Cl.
CPC ............ *A61M 5/3156* (2013.01); *A61M 5/20* (2013.01); *A61M 5/3155* (2013.01);
(Continued)

(58) Field of Classification Search
CPC .............. A61M 5/3156; A61M 5/3155; A61M 5/31553; A61M 2005/2026; A61M 5/31535

See application file for complete search history.

(56) References Cited

U.S. PATENT DOCUMENTS 5,104,380 A    4/1992 Holman et al.
6,004,297 A *  12/1999 Steenfeldt-Jensen ...................... A61M 5/31551
                                                    604/207
(Continued)

FOREIGN PATENT DOCUMENTS

JP    2005514120 A    5/2005
WO    2006045526 A1   5/2006
(Continued)

*Primary Examiner* — Bradley J Osinski
(74) *Attorney, Agent, or Firm* — Wesley Nicolas

(57) ABSTRACT

The invention relates to a torsion spring driven injection device having a dial-down mechanism for dialling down a selected dose size. The torsion spring (2) is strained when setting a dose by rotating a proximally located dose setting button(30) relatively to the housing in a first direction and unstained when rotating the same dose setting button (30) in a second direction opposite the first direction. In order to secure the torsion spring (2) in its strained position a one-way ratchet mechanism is provided. This one-way ratchet mechanism comprises a fixation element (1) coupled to the housing and having a toothing (6) and a ratchet element (20) having at least one ratchet arm (22) engaging the fixation element (1) and which ratchet element (20) is operational coupled to the dose setting button (30). The dose setting button (30) directly engages the at least one ratchet arm (22) when the dose setting button (30) is rotated in the second direction which releases the at least one ratchet arm (22) from the toothing (6) of the fixation element (1) and allows the ratchet element (20) to rotate relatively to the (Continued)

fixation element (1) in the second direction under influence of the torsion spring (2).

8 Claims, 3 Drawing Sheets

(52) U.S. Cl.
CPC ..... *A61M 5/31553* (2013.01); *A61M 5/31535* (2013.01); *A61M 2005/2026* (2013.01)

(56) References Cited

U.S. PATENT DOCUMENTS

| | | |
|---|---|---|
| 7,736,343 B2 | 6/2010 | Marshall et al. |
| 2008/0306445 A1 | 12/2008 | Burren et al. |
| 2012/0165752 A1* | 6/2012 | Holmqvist ........ A61M 5/31553 604/211 |

FOREIGN PATENT DOCUMENTS

| | | |
|---|---|---|
| WO | 2007063342 A1 | 6/2007 |
| WO | 2010046394 A1 | 4/2010 |
| WO | 2010089418 A2 | 8/2010 |
| WO | 2011025448 A1 | 3/2011 |
| WO | 2011154479 A1 | 12/2011 |
| WO | 2013098194 A2 | 7/2013 |

\* cited by examiner

DIAL-DOWN MECHANISM FOR WIND-UP PEN

CROSS-REFERENCE TO RELATED APPLICATIONS

This application is a 35 U.S.C. § 371 National Stage application of International Application PCT/EP2013/055403 (published as WO 2013/178372), filed Mar. 15, 2013, which claimed priority of European Patent Application 12170139.5, filed May 31, 2012; this application claims priority under 35 U.S.C. § 119 of U.S. Provisional Application 61/656,345; filed Jun. 6, 2012.

THE TECHNICAL FIELD OF THE INVENTION

The present invention relates to a torsion spring driven automatic injection device having a dial-down mechanism by which a user can dial down a dose size set to high. In particular, the present invention relates to a ratchet mechanism which can hold the force being accumulated in the torsion spring in one rotational direction and which ratchet can be actively released in a controlled manner to lower the force accumulated in the torsion spring.

DESCRIPTION OF RELATED ART

In known injection devices, such as wind-up pens, based on torsion springs, the user usually strains the torsion spring by rotating a rotatable and proximally provided dose setting button. The force thereby applied by the user is stored in the torsion spring for later release.

An example of a known wind-up pen applying a torsion spring may for example be found in U.S. Pat. No. 5,104,380. In this wind-up pen the dose setting member is located at the proximal end and works such that when the user rotates the dose setting member the spring is strained and maintained in this strained position until the user releases the set dose by activating the latch provided on the side of the housing. The wind-up pen disclosed in U.S. Pat. No. 5,104,380 has the disadvantage that if a user sets a dose to large it is not possible to decrease the set dose. The user then has to release the latch mechanism thereby expelling the entire set dose before a new correct dose can be set and delivered.

Wind-up pen in which the user can actually decrease the set dose prior to dosing is e.g. known from WO 2006/045526 and WO 2010/089418.

These automatic injection devices are based on a torsion spring which is tighten during dose setting and thereafter released to inject the set dose. If a user erroneously sets a dose higher than needed these injection devices has the possibility of lowering the set dose by rotating the dose setting member in an opposite rotational direction. Such dial-down mechanism can therefore save the user from expelling expensive drug due to an erroneous dose setting.

In WO 2006/045526, the dial-up/dial-down mechanism is based on a flexible ratchet arm which is locked in a one-way engagement with a toothed ring. When the user sets a dose he rotates the dose setting button provided at the proximal end of the injection device. This dose setting button is connected to the ratchet element via a longitudinal stretching tubular sleeve. The ratchet element is provided with a ratchet arm in a toothed engagement with the toothed ring such that the ratchet arm when the dose setting button is rotated locks against the force of the torsion spring in the subsequent teeth of the toothed ring thereby straining the torsion spring in incremental steps. In order to reduce the set size, the ratchet arm is actively pulled out of engagement with the toothed ring whereby the force accumulated in the torsion spring rotates the ratchet element rapidly backwards such that the ratchet arm engages the previous tooth in the toothed ring thereby lowering the set dose with one increment. Due to the presence of the longitudinal tube, it is possible to locate the ratchet mechanism away from the dose setting button e.g. in the proximity of the drive mechanism which is preferred when the side mounted latch mechanism engages directly on the drive mechanism.

A similar arrangement is disclosed in WO 2010/089418, however, in the dial-up/dial-down mechanism of this injection device depictured in FIG. 2, the toothed element securing the ratchet arm against the force of the torsion spring has outwardly pointing teeth and the ratchet arm points toward the center axis of the injection device. This construction also has the ratchet mechanism provided in the proximity of the drive mechanism which again is secured in its locked position by a latch mechanism provided on the side of the housing.

The dial-down arrangements know from WO 2006/045526 and WO 2010/089418 could be referred to as being active dial-down arrangements as the ratchet arm needs to be radially and actively pulled free of its toothed engagement in order to dial down the set dose size.

A dial-down mechanism which is not active is known from WO 2007/063342. In this arrangement as best seen in FIG. 12, a plurality of flexible arms engages the inside toothing of a drive gear thereby retaining the torsion spring in its strained position. These arms are flexible and can deflect radially inwardly when the user dials down the set dose without an additional element to release the arms.

A major problem in the prior art active dial-down mechanisms is that when the user dials down the set dose he actually releases the torsion spring by forcing the ratchet arm out of its engagement with the toothed element and the actual dial down i.e. the backward movement of the ratchet element is performed by the force of the torsion spring.

Automatic injection devices often operate with a pretensed torsion spring in order to operate in a range of the torsion spring characteristic where the torsion spring applies a relatively constant and a relatively large force.

This is particular troublesome when the dose setting button is connected to the ratchet mechanism via a longitudinal stretching sleeve element which also often are coupled in series with other elements. Once the torsion spring rotates back the ratchet element during dial down these elements can all vibrate under influence of the relative large force build up in the torsion spring. This vibration makes the dial down movement appear rather coarse and rough. The feel experienced by the user when rotating the dose setting member in the dialdown direction is therefore somewhat uncomfortable. Further, the vibrations generate unpleasant noises when dialing down.

One attempt to dampen this movement during dial down using friction is described in EP 11 195 986.2-2320.

DESCRIPTION OF THE INVENTION

It is an object of the present invention to provide a dial-up/dial-down mechanism for automatic wind-up pens which overcomes the above and provides a more smoothly impression when dialing down the set dose. A further object is to generate more space inside the housing for other components.

In a first embodiment, a torsion spring driven injection device having a dial-down mechanism for dialling down a selected dose size, comprises a torsion spring which is strained when setting a dose by rotating a proximally located dose setting button relatively to a housing in a first direction and unstrained when rotating the same dose setting button in a second direction opposite the first direction.

The dial-down mechanism further comprises:
a fixation element which is coupled to the housing and which fixation element has a plurality of teeth, and
a ratchet element having at least one ratchet arm engaging the fixation element in an one-way engagement.

More than one ratchet arm is allowed but at least one is required. The toothing on the fixation element can be provided either on the inside of the fixation element or on the outside as long as this toothing is engaged by the at least one of the ratchet arms.

The ratchet element carrying the at least one ratchet arm is coupled to the dose setting button, and follows the rotational movement of the dose setting button both when dialling up the dose and when dialling down the set dose.

Further, the at least one ratchet arm engages the teeth of the fixation element and is shaped such that the ratchet element is prevented from rotating relatively to the fixation element in the second direction when the ratchet arm engages the teeth of the fixation element. The dose setting button directly engages the at least one ratchet arm when the dose setting button is rotated in the second direction to thereby release the at least one ratchet arm from the teeth of the fixation element and allow the ratchet element to rotate relatively to the fixation element in the second direction preferably under influence of the torsion spring force.

By having the dose setting button being in direct contact with the ratchet arm it is secured that the part of the injection device which is firmly gripped by the user also is the element that controls the ratchet arm. Once the ratchet arm is moved out of engagement with the teeth of the fixation element, the torsion spring is released and moves the ratchet element with the ratchet arm backward to engage the previous teeth. At the end of this backward movement, the ratchet arm will impact the fixation element. Since the ratchet element is provided directly between the fixation element and the dose setting button, the impact will be dampen by the users own hand holding the dose setting button. Each flexible ratchet arm is preferably but not necessarily provided with one teeth having an abrupt end engaging the toothing of the fixation element. The abrupt end can also be provided directly at the end of the flexible ratchet arm.

The fixation element can either be a part of the drive mechanism as disclosed in WO 2006/045526 and WO 2010/089418 or it can be firmly attached to the housing e.g. being an integral part of the housing.

When the fixation element is permanently secured to the housing, the fixation element is non-rotatable in all situation i.e. also during ejection. The torsion spring is usually provided between the housing and a rotatable part of the drive mechanism. In order for the torsion spring to release its accumulated force, the rotatable drive mechanism must be temporary separated from the fixation element and the ratchet element during dosing.

Alternatively the torsion spring rotates both the fixation element and the ratchet element which then during ejection must be released from the housing.

The teeth of the fixation element is preferably V-shaped with a steep side abutting an abrupt end of the at least one ratchet arm such that the ratchet arm and the ratchet element is effectively prevented form rotating relatively to the fixation element without the ratchet arm being actively released from the V-shaped teeth.

In the axial direction of the injection device, the ratchet element protrudes above the fixation element such that the ratchet element and in particular the at least one ratchet arm can be easily engaged by the dose setting member. In order to accommodate the engagement with the dose setting button, the ratchet element is provided at the proximal end of the injection device.

The dose setting button is, preferably on its inner surface, provided with a first protrusion, or first set of protrusions, which engage the ratchet element when the dose setting button is rotated in the dose setting direction. Due to this engagement, the ratchet element rotates together with the dose setting button when a dose is being set. At the same time the ratchet arm clicks over the teeth providing a distinct sound of one click per teeth. Further this rotation strains the torsion spring.

The second protrusion engages the ratchet arms when dialling in the opposite direction i.e. when dialling down the set dose size.

The second protrusion is preferably shaped such that it can move the ratchet arm in the radial direction when rotated relatively to the ratchet arm and the ratchet element.

Further, the second protrusion is preferably shaped such that at least a part of the second protrusion lies in front of the abrupt end of the ratchet arm at least when dialling down the set dose. In this case the ratchet arm will not be hammered against the bottom of the V-shaped teeth when the ratchet arm is lifted over into the adjacent tooth (or rather the valley between the teeth) but will instead be gripped by the part of the second protrusion extending in front of the ratchet arm and more softly be guided down to the bottom of the V-shaped teeth.

I.e. the second protrusion carried by the dose setting button has a double function. When dialing down i.e. in the second direction it operates the ratchet arm to release the ratchet arm from the teeth of the fixation element e.g. by operating the ratchet arm in a radial direction out of its engagement, and at the same time it is structured such that it grips the ratchet arm when the abrupt end of the ratchet arm is moved back over the adjacent teeth and into the neighbouring valley.

The second protrusion is preferably provided with an upper surface designed to catch the ratchet arm when the dose setting button is rotated in the second direction in order to reduce the set dose. The upper surface catching the ratchet arm can have any shape accommodating the ratchet arm. Preferably the second protrusion and the ratchet arm have similar engaging shapes e.g. a sloping surface. Important is that the ratchet arm is both moved out of engagement with the tooth and guided into the adjacent valley by the second protrusion simultaneously. The second protrusion being a part, preferably an integral part (e.g. moulded together), of the dose setting button. The first element that the ratchet arm encounters when released is thus the second protrusion which again is a part of the dose setting button which is dampened by the contact with the users fingers.

The second protrusion with its double function could also be designated as a release protrusion since the first protrusion is not absolutely necessary. The dose dial button can be provided with other means than a first protrusion for driving the ratchet element in the first direction. The mechanism for driving in the first direction could e.g. be part of the centre connection between the ratchet element and the dose setting button.

In e.g. WO 2011/025448 the ratchet arm is only moved over the teeth by the release arm. There is no mechanism to grip the ratchet arm resulting in the ratchet arm hammering against the bottom of the ring-shaped element without any dampening. The noise is thus carried directly to the housing.

DEFINITIONS

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

The term "Needle Cannula" is used to describe the actual conduit performing the penetration of the skin during injection. A needle cannula is usually made from a metallic material such as e.g. stainless steel and connected to a hub to form a complete injection needle also often referred to as a "needle assembly".

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device to which the needle assembly is attached whereas the term "proximal end" is meant to refer to the opposite end holding the dose setting button.

Figure 1:
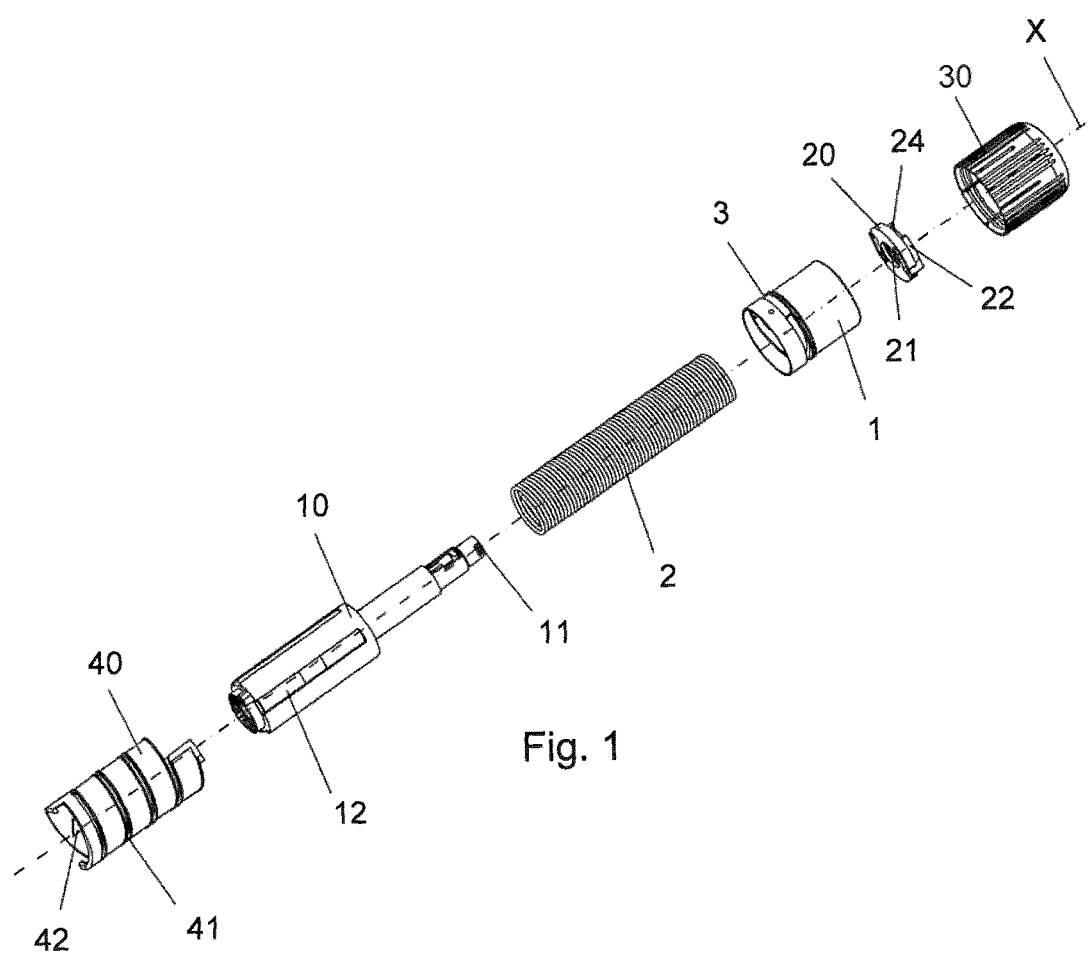
FIG. 1 shows an exploded view of the dose setting mechanism.

The dose dial mechanism is shown in an exploded view in FIG. 1. A spring base or fixation element 1 secures a torsion spring 2. This fixation element 1 has a circumferential extension 3 which is press fitted into a non-shown housing such that the fixation element 1 is permanently and non-rotatable fixed to the housing. The fixation element 1 further holds the proximal end of a torsion spring 2 such that the proximal end of the torsion spring 2 is locked to the housing. The opposite distal end of the torsion spring 2 is secured to a drive tube 10 such that when the drive tube 10 is rotated in the clock-wise direction, the torsion spring 2 is tightened.

The drive tube 10 is proximally provided with a toothing 11 engaging a similar toothing 21 on the ratchet element 20 such that when the ratchet element 20 is rotated the drive tube 10 rotates with it. Most proximally the ratchet element 20 is connected to the dose setting button 30 as will be explained below.

In order to visually indicate the size of the dose being set when rotating the dose setting button 30, the drive tube 10 is connected to a scale drum 40 by having a groove 12 being engaged by a corresponding raised bar 42 internally in the scale drum 30. The scale drum 40 can in this way slide axially relatively to the drive tube 10 but are forced to rotate with the drive tube 10. On its outside surface the scale drum 40 is provided with a helical track 41 threaded to the not-shown housing. Once the user rotates the dose setting button 30 and in turn the ratchet element 20 and the drive tube 10 (via the toothing 11/21), the torsion spring 2 is strained and the scale drum 40 moves helically due to its groove connection with the drive tube 10.

In order to release the strained torsion spring 2 and eject the set dose, the ratchet element 20 and the drive tube 10 are moved axially in relation to each other such that the toothing 11 of the drive tube 10 disengages the toothing 21 of the ratchet element 20 whereby the force accumulated in the torsion spring 2 during dose setting is released and rotates the drive tube 10 rotational back to its initial position. The drive tube 10 is further connected to a not-shown injection mechanism such that the set dose of drug is expelled during this backwards rotation of the drive tube 10. The injection mechanism further includes a cartridge containing the liquid drug which is pressed out through a distally provided injection needle.

Figure 2:
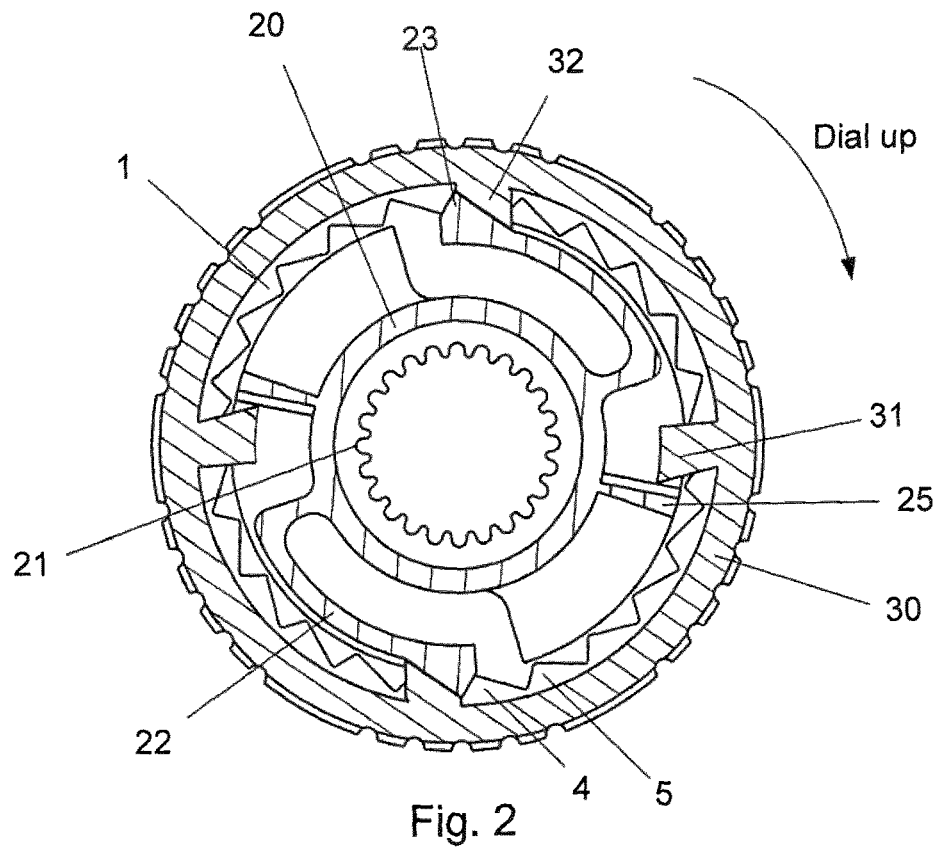
FIG. 2 shows a cross-sectional view through the proximal end of the injection device in the dial-up mode.
Figure 3:
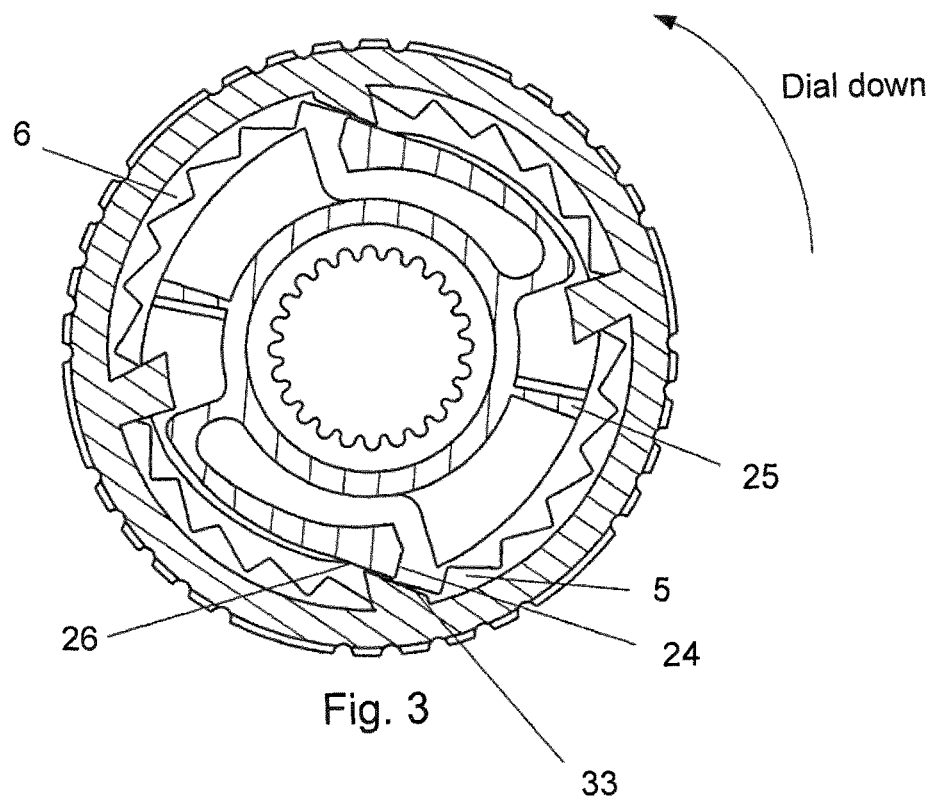
FIG. 3 shows a cross-sectional view through the proximal end of the injection device in the dial-down mode.

The engagement between the dose setting button 30 and the ratchet element 20 is further shown in FIG. 2 and FIG. 3. The ratchet element 20 with its centrally located toothing 21 is in this embodiment provided with two identical flexible ratchet arms 22, each carrying a tooth 23 having an abrupt end 24. This abrupt end 24 engages a V-shaped teeth 4 of a proximal and internal toothing 6 provided on the fixation element 1 such that the ratchet arm 22 and the ratchet element 20 can only rotate in one direction (clock-wise in FIG. 2) in relation to the fixation element 1.

To drive the rotation of the ratchet element 20 during dose setting, the dose setting button 30 is provided with a first protrusion 31 which abuts the ratchet element 20 when the dose setting button 30 is rotated in the dose setting direction (clock-wise in FIG. 2).

The ratchet element 20 is provided with a surface 25 which is abutted by the first protrusion 31. This surface 25 and the first protrusion 31 can be provided in pairs as depictured in FIGS. 2 and 3. This surface 25 together with the ratchet arms 22 is proximally raised in relation to the remaining part of the ratchet element 20 such that the surface 25 and the ratchet arms 22 lies above the proximal edge of the fixation element 1 when viewed in an axial direction. This is clear from FIG. 1 and serves the purpose of enhancing the engagement with the various protrusions inside the dose setting button 30 as explained in the following.

The dose setting button 30 is further provided with a second protrusion 32 having a steep upper surface 33. This upper surface 33 rest against a similar surface 26 on the ratchet arm 22. Once the user rotates the dose setting button 30 to lower the set dose as depictured in FIG. 3, this steep upper surface 33 forces the ratchet arm 22 in a radial inwardly direction such that the abrupt end 24 is lifted radially out of its engagement with the V-shaped teeth 4.

Following this, the torsion spring 2 will urge the ratchet element 20 rotational in the counter clock-wise direction (in FIG. 3) and the abrupt end 24 of the ratchet arm 22 will engage the previous V-shaped teeth 5 and be arrested there. The result being that the set dose has been decreased with one increment. Further counter clock-wise rotation of the dose setting button 30 will result in the dose being further decreased.

As any random number of flexible ratchet arms 22 can be provided, a similar number of second protrusions 32 are favoured, one for each ratchet arm 22.

Figure 4:
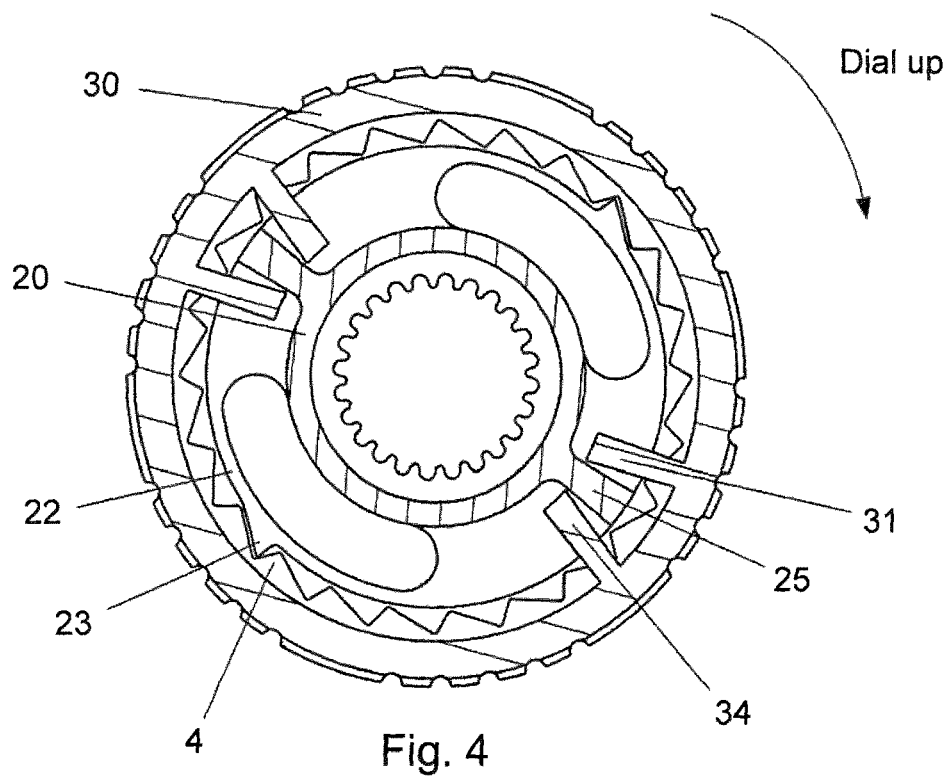
FIG. 4 shows a cross-sectional view of a different embodiment of the injection device in the dial-up mode.
Figure 5:
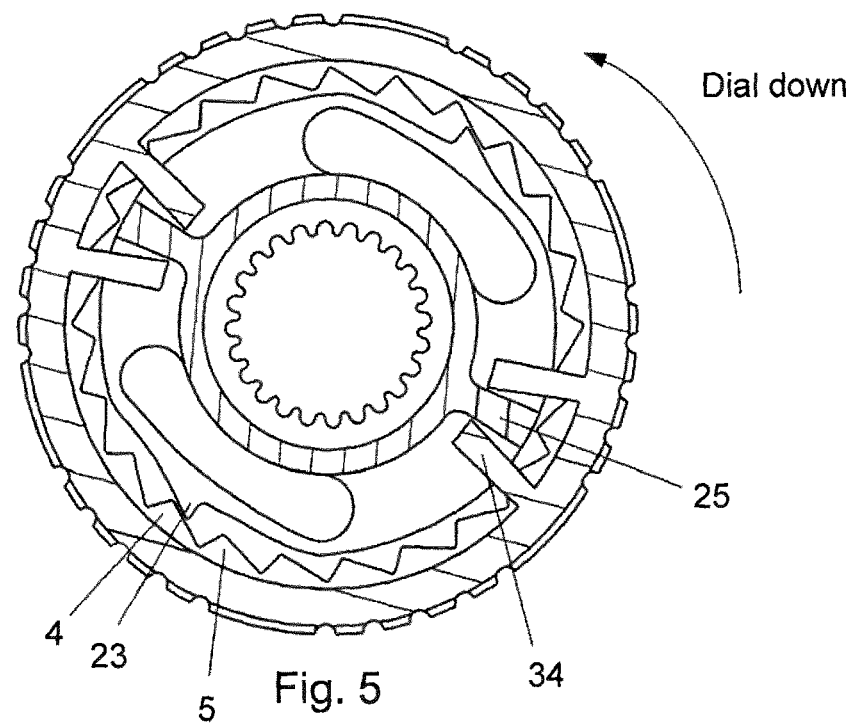
FIG. 5 shows a cross-sectional view of a different embodiment of the injection device in the dial-down mode.

FIG. 4 and FIG. 5 shows an embodiment in which the ratchet arm 22 is not active, somewhat similar to the disclosure of WO 2007/063342.

In this embodiment, the dose setting button 30 is provided with an additional protrusion 34 which abuts the surface 25 on the ratchet element 20 when dialling down the set dose as depictured in FIG. 5. When dialling up the dose as in FIG. 4, the protrusion 31 abuts the surface 25.

The ratchet arm 22 is constructed somewhat like a bridge or beam and is able to bend inwardly in a radial direction when the dose setting button 30 is dialled down such that the tooth 23 can slip over and into engagement with the previous V-shaped teeth 5 of the fixation element 1 as indicated in FIG. 5.

Some preferred embodiments have been shown in the foregoing, but it should be stressed that the invention is not limited to these, but may be embodied in other ways within the subject matter defined in the following claims.

The invention claimed is:

1. A injection device having a dial-down mechanism for dialling down a selected dose size, comprising a dose setting button having an inner circumference and an outer circumference and a torsion spring which is strained when setting a dose by rotating the dose setting button relative to a housing in a first direction and unstrained when rotating the same dose setting button in a second direction opposite the first direction, the dial-down mechanism further comprising:
   a fixation element permanently coupled to the housing and having a toothing,
   a ratchet element provided in the proximal end of the injection device having at least one ratchet arm engaging the fixation element and which ratchet element is operationally coupled to the dose setting button, and
   wherein the at least one ratchet arm engages the toothing of the fixation element and is shaped such that the ratchet element is prevented from rotating relatively to fixation element in the second direction when the ratchet arm engages the toothing of the fixation element, and wherein the dose setting button directly engages the at least one ratchet arm when the dose setting button is rotated in the second direction to thereby release the at least one ratchet arm from the toothing of the fixation element and allow the ratchet element to rotate relatively to the fixation element in the second direction under influence of the torsion spring, and
   wherein the inner circumference of the dose setting button has a release protrusion engaging the ratchet arm when the dose setting button is rotated in the second direction, such that
   the release protrusion moves the ratchet arm in an approximate radial direction to release the ratchet arm from the fixation element thereby allowing the torsion spring to rotate the ratchet element in the second direction.

2. An injection device having a dial-down mechanism according to claim 1, wherein the teeth of the fixation element are V-shaped.

3. An injection device having a dial-down mechanism according to claim 1, wherein the at least one ratchet arm has an abrupt end engaging one of the V-shaped teeth of the fixation element.

4. An injection device having a dial-down mechanism according to claim 1, wherein the ratchet element protrudes above and beyond the fixation element in the axial direction.

5. An injection device having a dial-down mechanism according to claim 1, wherein the dose setting button has a first protrusion engaging the ratchet element when the dose setting button is rotated in the first direction to set a dose.

6. An injection device having a dial-down mechanism according to claim 1, wherein at least a part of the release protrusion is positioned such that the ratchet arm abuts the release protrusion when released.

7. An injection device having a dial-down mechanism according to claim 6, wherein the at least part of the release protrusion is positioned in front of an abrupt end of the ratchet arm when the ratchet arm is released as the dose setting button is rotated in the second direction.

8. An injection device having a dial-down mechanism according to claim 1, wherein the release protrusion has an upper surface designed to catch the ratchet arm when the dose setting button is rotated in the second direction.

* * * * *